United States Patent
Lisonbee et al.

(10) Patent No.: US 11,197,894 B2
(45) Date of Patent: *Dec. 14, 2021

(54) NANOFRACTION IMMUNE MODULATORS, PREPARATIONS AND COMPOSITIONS INCLUDING THE SAME, AND ASSOCIATED METHODS

(71) Applicant: 4Life Patents, LLC, Sandy, UT (US)

(72) Inventors: David A. Lisonbee, Orem, UT (US); Calvin W. McCausland, Springville, UT (US); Richard H. Bennett, Captain Cook, HI (US); Brent M. Vaughan, Draper, UT (US); Shane M. Lefler, American Fork, UT (US)

(73) Assignee: 4Life Patents, LLC, Sandy, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/679,908

(22) Filed: Nov. 11, 2019

(65) Prior Publication Data

US 2020/0069737 A1   Mar. 5, 2020

Related U.S. Application Data

(63) Continuation of application No. 11/855,944, filed on Sep. 14, 2007, now Pat. No. 10,471,100.

(60) Provisional application No. 60/848,348, filed on Sep. 29, 2006.

(51) Int. Cl.
| | |
|---|---|
| *A61K 35/20* | (2006.01) |
| *A61K 35/57* | (2015.01) |
| *G01N 33/50* | (2006.01) |
| *A23L 33/10* | (2016.01) |
| *A23L 33/17* | (2016.01) |

(52) U.S. Cl.
CPC ............ *A61K 35/20* (2013.01); *A23L 33/10* (2016.08); *A23L 33/17* (2016.08); *A61K 35/57* (2013.01); *G01N 33/505* (2013.01); *G01N 2333/70514* (2013.01)

(58) Field of Classification Search
None
See application file for complete search history.

(56) References Cited

U.S. PATENT DOCUMENTS

| | | | |
|---|---|---|---|
| 4,402,938 A | | 9/1983 | Collins et al. |
| 4,816,563 A | | 3/1989 | Wilson et al. |
| 5,585,098 A | | 12/1996 | Coleman |
| 5,773,232 A | | 6/1998 | Wier |
| 6,630,316 B1 | | 10/2003 | Wier |
| 6,866,868 B1 * | | 3/2005 | Lisonbee ............... A61K 35/20 424/535 |
| 7,094,415 B2 | | 8/2006 | Marenick |
| 7,169,571 B2 | | 1/2007 | Wier |
| 10,464,980 B2 * | | 11/2019 | Lisonbee ............... C07K 14/52 |
| 10,471,100 B2 * | | 11/2019 | Lisonbee ............... A61P 37/02 |
| 2002/0044942 A1 | | 4/2002 | Dopson |
| 2003/0152641 A1 | | 8/2003 | Iyer et al. |
| 2004/0005327 A1 | | 1/2004 | Iyer et al. |
| 2005/0058716 A1 | | 3/2005 | Lisonbee et al. |
| 2005/0260563 A1 | | 11/2005 | Wier |

FOREIGN PATENT DOCUMENTS

| | | | | |
|---|---|---|---|---|
| AU | 2007305076 B2 | | 4/2008 | |
| CN | 1460522 A | | 12/2003 | |
| CN | 1762391 A | | 4/2006 | |
| CO | 5418 | | 9/2013 | |
| EP | 0914831 | * | 5/1999 | ............ A61K 39/42 |
| EP | 2068913 B1 | | 11/2017 | |
| HK | 1138181 B | | 8/2010 | |
| IN | 300928 | | 9/2007 | |
| JP | 60-208919 | | 10/1985 | |
| JP | 2010-504988 A | | 2/2010 | |
| JP | 5592651 B2 | | 9/2014 | |
| JP | 6401744 B2 | | 10/2018 | |
| MX | 302235 | | 9/2007 | |
| RU | 2518341 C2 | | 6/2014 | |

(Continued)

OTHER PUBLICATIONS

Kruzel et al, Journal of Molecular Neuroscience, 2001, vol. 17, pp. 379-389. (Year: 2001).*

Bacsi et al, Cellular and Molecular Neurobiology, 2005, 25(7):1123-1139. (Year: 2005).*

Allergyresearchgroup "Cytolog Spray product sheet," Retrieved from the Internet Jul. 10, 2012: <VEL: http://www.freedomfromme.co.ukldocs/CytologProductSheetpdf>.

Danish Patent and Trademark Office, "Singapore Search Report and Written Opinion," dated Jul. 11, 2014, in related in Singapore Patent Application No. 2013095435.

(Continued)

*Primary Examiner* — Allison M Fox
(74) *Attorney, Agent, or Firm* — Dentons Durham Jones Pinegar

(57) ABSTRACT

Compositions that include extracts from sources of immune modulators that include nanofraction immune modulator molecules (i.e., molecules having molecular weights of about 3,000 Da and less) are disclosed. These compositions may also include other immune modulators, such as transfer factor. Administration of compositions with extracts that include nanofraction immune modulator molecules modulates the cell-mediated immunity (e.g., down-regulates undesired T cell activity) of a subject to which such compositions are administered. When administered with transfer factor, the combination of nanofraction immune modulator molecules and transfer factor down-regulates undesired T cell activity while increasing, or up-regulating, T cell activity against pathogens and other undesirable entities, such as cancer cells and other aberrant or mutated cells. Assays and assay techniques for evaluating the immune modulation capabilities of various substances are also disclosed.

7 Claims, 4 Drawing Sheets

(56) References Cited

FOREIGN PATENT DOCUMENTS

| | | |
|---|---|---|
| RU | 2619555 C2 | 5/2017 |
| SG | 151421 | 4/2010 |
| SG | 160430 A1 | 4/2014 |
| TH | 65016 B | 9/2018 |
| TW | I449530 B | 8/2014 |
| WO | 1997/035595 A1 | 10/1997 |
| WO | 2002/024746 A1 | 3/2002 |
| WO | 2002/038164 A1 | 5/2002 |
| WO | 2004041071 A2 | 5/2004 |
| WO | 2005028622 A2 | 3/2005 |

OTHER PUBLICATIONS

European Patent Office, "Supplementary European Search Report," dated Nov. 4, 2009, in European Application No. 07814934.1.

Fabre, RA, et al., "Transfer factors as immunotherapy and supplement of chemotherapy in experimental pulmonary tuberculosis," Clin Exp Immunol 136:215-223 (2004).

Ferdinandi, ES, et al., "Virulizin®—A review of its antineoplastic activity," Exp Opin Invest Drugs, 8(10):1721-1735 (1999).

Siemion, IZ, et al., "Peptides related to the active fragment of 'proline-rich polypeptide', an immunoregulatory protein in the ovine colostrum," Int J Pept Prot Res 36:506-514 (Jun. 9, 1990).

USPTO as International Searching Authority, "International Search Report," International Application No. PCT/US2007/078947, dated Aug. 22, 2008.

Japan Patent Office, "Notification of Decision of Rejection," Japanese Application No. 2014-046094, dated Feb. 22, 2016.

Japan Patent Office, "Notification of Reasons for Rejection," Japanese Application No. 2014-046094, dated Apr. 22, 2015.

Staroscik, K, et al., "Immunologically active nonapeptide fragment of proline rich polypeptide from ovine colostrum: amino acid sequence and immunoregulartory properties," Mol Immunol 20(12):1277-1282 (May 18, 1983).

Mincheva-Nilsson, L, et al., "Human milk contains proteins that stimulate and suppress T lymphocyte proliferation," Clin Exp Immunol 79(3):463-469 (1990).

Nitsch, AD, et al., "The clinical use of bovine colostrum," J Orthomolecular Med 13(2):110-118 (1998).

Patent Office of the Russian Federation, "Official Action," Russian Application No. 2014102562, dated May 20, 2016.

Patent Office of the Russian Federation, "Official Action," Russian Application No. 2014102562, dated Sep. 2, 2015.

Rozzo, SJ, et al., "Purification of Transfer Factors," Mol Immunol 29(2):167-182 (1992).

"Science of Milk (Nyu no Kagaku)," pp. 111-121 (1998).

Sottong, PR, et al., Measurement of T-lymphocyte responses in whole-blood cultures using newly synthesized DNA and ATP, Clinical and Diagnostic Laboratory Immunology, Mar. 2000, vol. 7, No. 2, p. 307-311.

State Intellectual Property Office of the People'S Republic of China, "Search Report," dated Nov. 5, 2013, in related Chinese Application No. 200780039690.X.

Sugisawa, H. et al., A low-molecular-weight fraction of bovine colostrum and milk enhances the oxidative burst activity of polymorphonuclear leukocytes, Vet Res Commun 27(6):453-461 (2003).

Taiwan Intellectual Property Office, "Examination Report and Search Report," Taiwan Application No. 96135902, dated Oct. 12, 2009.

European Patent Office, "Communication pursuant to Article 94(3) EPC," European Application No. 07814934.1, dated Oct. 4, 2013.

European Patent Office, "Communication pursuant to Article 94(3) EPC," European Application No. 07814934.1, dated Jul. 2, 2014.

European Patent Office, "Communication pursuant to Article 94(3) EPC," European Application No. 07814934.1, dated Feb. 19, 2015.

State Intellectual Property Office of China, "First Office Action," Chinese Application No. 200780039690.X, dated Aug. 3, 2011.

State Intellectual Property Office of China, "Second Office Action," Chinese Application No. 200780039690.X, dated Sep. 4, 2012.

State Intellectual Property Office of China, "Final Rejection," Chinese Application No. 200780039690.X, dated Apr. 15, 2013.

State Intellectual Property Office of China, "Re-Examination Decision," Chinese Application No. 200780039690.X, dated Aug. 14, 2013.

State Intellectual Property Office of China, "Fourth Office Action," Chinese Application No. 200780039690.X, dated Aug. 7, 2014.

Japan Patent Office, "Notification of Reasons for Rejection," Japanese Application No. 2009-530527, dated Jul. 23, 2012.

Japan Patent Office, "Notification of Reasons for Rejection," Japanese Application No. 2009-530527, dated Mar. 22, 2013.

Japan Patent Office, "Final Rejection," Japanese Application No. 2009-530527, dated Nov. 8, 2013.

Intellectual Property Corporation of Malaysia, "Substantive Examination Adverse Report," Malaysian Application No. PI20091276, dated May 15, 2013.

Intellectual Property Corporation of Malaysia, "Substantive Examination Adverse Report," Malaysian Application No. PI20091276, dated Jan. 30, 2014.

Intellectual Property Corporation of Malaysia, "Substantive Examination Clear Report," Malaysian Application No. PI20091276, dated Apr. 15, 2016.

Intellectual Property Corporation of Malaysia, "Substantive Examination Adverse Report," Malaysian Application No. PI2013003021, dated Jan. 15, 2018.

\* cited by examiner

NANOFRACTION IMMUNE MODULATORS, PREPARATIONS AND COMPOSITIONS INCLUDING THE SAME, AND ASSOCIATED METHODS

CROSS-REFERENCE TO RELATED APPLICATION

This application is a continuation of U.S. patent application Ser. No. 11/855,944, filed Sep. 14, 2007, titled NANOFRACTION IMMUNE MODULATORS, PREPARATIONS AND COMPOSITIONS INCLUDING THE SAME, AND ASSOCIATED METHODS ("the '944 Application"), now U.S. Pat. No. 10,471,100, issued Nov. 12, 2019. The '944 Application includes a claim for priority to the Sep. 29, 2006 filing date of U.S. Provisional Patent Application No. 60/848,348 ("the '348 Provisional Application") under 35 U.S.C. § 119(e). The entire disclosures of the '348 Provisional Application and the '944 Application are hereby incorporated herein.

TECHNICAL FIELD

The present invention relates to molecules that modulate (e.g., elicit, enhance, suppress undesirable activity, etc.) cell-mediated immunity in a subject, including methods for generating and obtaining such molecules, preparations and compositions that include such molecules, methods for evaluating the effectiveness of such molecules, and methods of use. More specifically, the present invention relates to small molecules, which are referred to herein as "nanofraction" molecules that modulate cell-mediated immunity.

RELATED ART

The ability of antibodies to provide and transfer immunity is well known and widely researched, as are the characteristics of antibodies and the mechanisms by which antibodies are produced.

Not so well known or so widely researched are the roles transfer factors, which includes a family of molecules having molecular weights of between 3,500 Da and 7,500 Da, play in modulating cellular, or T-cell-mediated, immunity. Over time, the understanding that those of skill in the pertinent art have about the characteristics of transfer factors and their roles in an organism's immune system has improved and continues to improve.

While further research continues to shed light on the characteristics and functions of a wide variety of immune system components, there may be a large number of poorly understood, or even overlooked molecules that may have an impact on the manner in which immunity is developed, maintained, conveyed, and transferred, as well as on the effects of immunity on longevity.

SUMMARY

The effectiveness of various molecules in modulating cell-mediated immunity has recently been characterized in a quantifiable manner. Molecules that may directly or indirectly modulate cell-mediated immunity are known in the art as "immune modulators." One class of immune modulators includes small, or low molecular weight, nanofraction (e.g., up to 3,000 Da, up to 3,500 Da, 250 Da to 2,000 Da, 2,000 Da to 4,000 Da) molecules that elicit, enhance, suppress, or otherwise modulate a cell-mediated immune response. Due to the relatively small sizes, or molecular weights, of such immune modulators, they are referred to herein as "nanofraction" immune modulators and as "nanofraction" molecules.

Nanofraction immune modulators may be obtained from a variety of different types of source animals. Examples of source animals include, but are not limited to, mammals (e.g., cows) and birds (e.g., chickens). Without limiting the scope of the present invention, nanofraction immune modulators may be obtained from colostrum, or even milk, produced by a mammal. As another non-limiting example, nanofraction immune modulators may be acquired from eggs produced by birds or any other type of animal. Colostrum, eggs, and other sources of nanofraction molecules are collectively referred to herein as "nanofraction sources."

The natural production of nanofraction immune modulators by a source animal may be enhanced by exposing the source animal to a greater amount, or concentration, of one or more antigens than the amount(s) of such antigen(s) to which the source animal would normally be exposed. For example, if a particular type of source animal, or even a specific source animal, would, in its typical environment, normally be exposed to a certain amount or concentration of a given antigen, the source animal's production of immune modulators, including nanofraction molecules, may be enhanced by exposing the source animal to an even greater amount (e.g., concentration) of that antigen (e.g., by vaccinating the source animal, by placing the source animal into an environment where a greater amount or concentration of that antigen is present, etc.). As another example, if a particular type of source animal, or even a specific source animal, were typically vaccinated with a given antigen, the source animal's production of one or more nanofraction immune modulators could be enhanced by increasing the exposure of the source animal to an antigen (e.g., by exposing the source animal to an increased concentration of the antigen, a more effective or more virulent form of the antigen, etc.), although the nanofraction molecules are not themselves believed to be antigen specific.

Known processes may be used to partially, substantially, or completely purify nanofraction immune modulators from other molecules present in the nanofraction source animal from which they are obtained and, optionally, to concentrate the nanofraction immune modulators. Such processes include, without limitation, mechanical separation, phase separation (e.g., separation of aqueous and non-aqueous components from one another), precipitation, centrifugation, filtration (including microfiltration, with a molecule weight cutoff (MWCO) in the range of about 12,000 Da down to about 4,000 Da, and nanofiltration, with an MWCO of less than about 4,000 Da), dialysis, chromatographic, and electrophoretic purification processes. Such processes may be effected individually or in any combination to produce a preparation in which one or more types of immune modulators are present.

In one aspect, the present invention includes preparations of at least partially purified, substantially purified (e.g., to a degree accepted by those in the pertinent art), and completely purified immune modulators. Additionally, the present invention includes compositions that include nanofraction molecules. In addition to nanofraction molecules, such compositions may include other components that are useful in supporting or modulating the immune system of a subject (e.g., transfer factor, antibodies, etc.), as well as components that may benefit the subject in other ways.

Methods that include use or administration of nanofraction molecules or compositions including the same, alone or with other immune modulators, are also within the scope of the present invention. Methods of use include the administration of one or more types of immune modulators (e.g., in raw, partially purified, substantially purified, or completely purified form, in a preparation, in a composition, etc.) to a subject (e.g., a human or any type of animal that is believed to benefit from the immune modulation provided by nanofraction molecules). The immune modulators are administered to a subject in an amount that increases the level (e.g., concentration) of a particular, administered type of immune modulator in the body of the subject to an above-normal amount for the subject. Without limiting the scope of this aspect of the present invention, a subject may receive an amount of one or more immune modulators that is clinically effective for causing the immune system of the subject to elicit a cell-mediated immune response or an amount that effectively enhances a cell-mediated immune response by the subject.

In addition, tests and testing methods that evaluate the effectiveness of immune modulators are within the scope of the present invention. As an example, a T-cell immune function assay may be used to evaluate the ability of a potential immune modulator to modulate the activity of (e.g., production of adenosine tri-phosphate (ATP) by) one or more types of cells that participate in cell-mediated immunity, either alone or in conjunction with other molecules (e.g., antigens, mitogens (which induce mitosis, or cell replication, etc.).

Other features and advantages will become apparent to those of skill in the art through consideration of the ensuing description and the appended claims.

DETAILED DESCRIPTION

Figure 1:
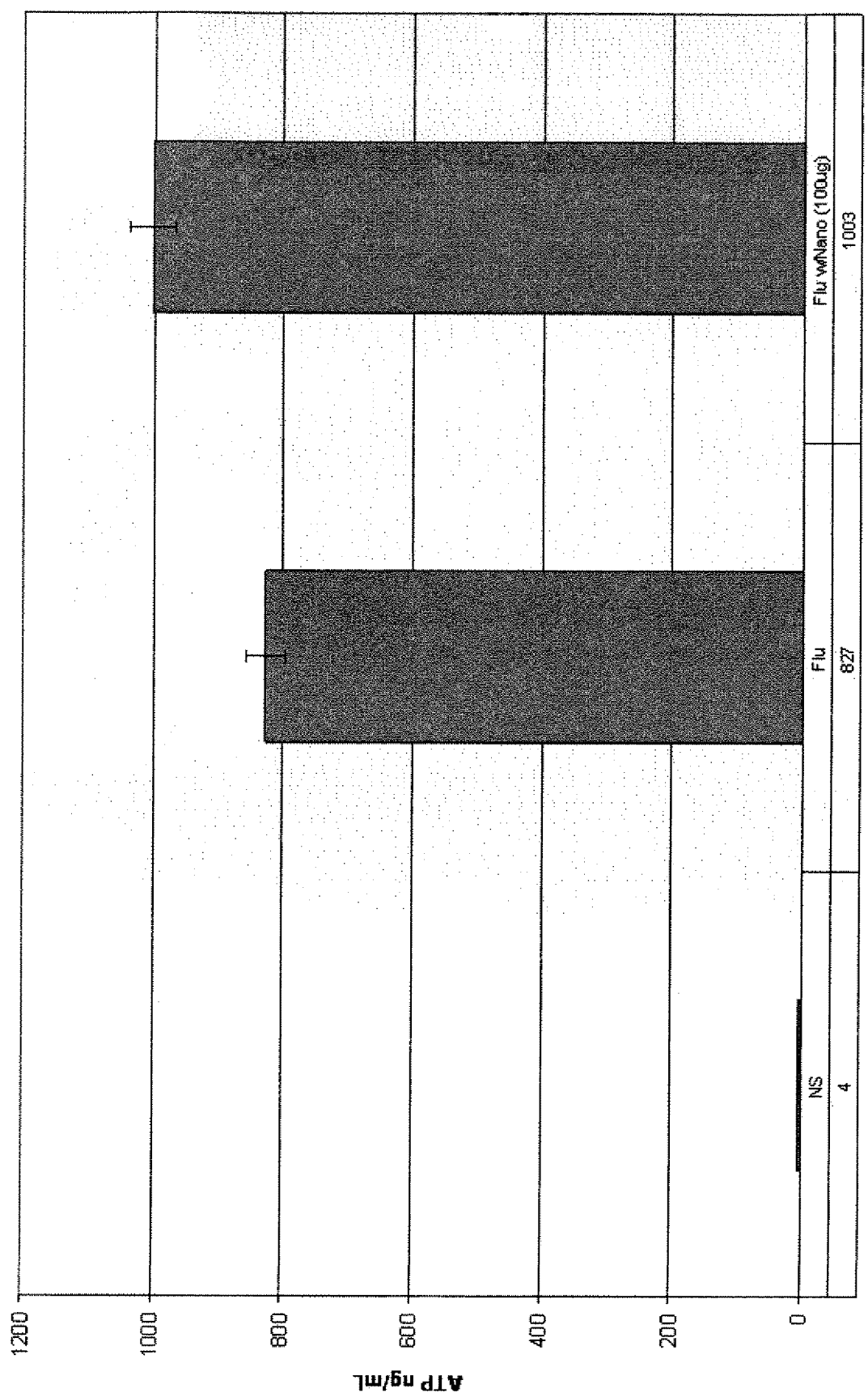
FIGS. 1 through 4 are graphic illustrations of the results of various tests performed on compositions that incorporate teachings of the present invention.

It has recently been discovered that small molecules in a variety of molecular weight ranges are useful in modulating the activity of immune cells. The following EXAMPLES set forth the acts that were performed to reach these conclusions.

Example 1

Using known processes, including phase separation, precipitation, filtration, microfiltration or nanofiltration, and dialysis, a variety of molecular weight fractions were prepared from both bovine colostrum and chicken eggs. The molecular weight fractions that were obtained from bovine colostrum were: 250 Da to 2,000 Da, 2,000 Da to 4,000 Da, 4,000 Da to 8,000 Da (which includes transfer factor, and was included for the sake of comparison), and 8,000 Da to 12,000 Da. Similarly, 2,000 Da to 4,000 Da, 4,000 Da to 8,000 Da (which includes transfer factor, and was included for the sake of comparison), and 8,000 Da to 12,000 Da molecular weight fractions were prepared from chicken egg yolks. The molecular weight fractions were then dried to powder form (e.g., by spray drying, freeze drying, etc.).

Various assays were then conducted using these preparations to evaluate the effects of molecules in each fraction to modulate the activity of cells that convey cellular immunity (e.g., CD4+ T helper cells). Specifically, assays of the type disclosed in U.S. Pat. Nos. 5,773,232 and 6,630,316 and in U.S. Patent Application Publication 2005/0260563, the entire disclosure of each of which is hereby incorporated herein, in its entirety, by this reference, were modified and used to evaluate the activities of different molecular weight fractions from EXAMPLE 1 in a variety of conditions. The aforementioned assays are used to evaluate the production of adenosine tri-phosphate (ATP) by immune cells (e.g., CD4+ T helper cells, CD3+ cells (which includes all T-cells), etc.). The amount of ATP produced by the cells may be measured in a manner known in the art (e.g., by use of the so-called "Luciferin reaction" with a lumenometer).

Example 2

A first series of assays was conducted using the white blood cells of healthy individuals that include, or express, so-called "CD4" glycoproteins on their surfaces using the ImmuKnow™ assay produced by Cylex Incorporated of Columbia, Md. These white blood cells are also referred to as "CD4+" cells due to their expression of the CD4 glycoproteins. Expression of the CD4 glycoprotein distinguishes so-called "T helper" cells from other types of white blood cells, including other T-cells.

The components of the ImmuKnow™ assay test kit were: a standard 96-well "Assay Plate," including removable eight well strips; a "Sample Diluent," which includes growth medium and a preservative; a "Stimulant," which includes phytohemagglutinin-L (PHA-L) (a substance from beans (e.g., red kidney beans) that is known to nonspecifically stimulate mitosis (a process in which a cell grows and splits into two new cells) and, thus, the preparatory production of adenosine tri-phosphate (ATP) in white blood cells (i.e., a "mitogen")), introduced into the remaining four "stimulated" wells of the eight well strip, diluted in growth medium and a preservative; "Dynabeads®* CD4," which are magnetic sample purification beads coated with mouse monoclonal anti-human CD4 antibodies and are carried by a buffered saline solution with bovine serum albumin (BSA) and preservative; a "Wash Buffer," which includes a buffered saline solution with BSA; a "Lysis Reagent," which includes a hypotonic basic solution with detergent, a "Calibrator Panel" with ATP concentrations of 0, 1, 10, 100, and 1,000 ng/ml; a "Luminescence Reagent" including luciferin and luciferase in a buffered solution, which reacts with ATP to create light in an amount indicative of the amount of ATP to which the Luminescence Reagent has been exposed; and a "Measurement Plate" with 96 wells that have opaque boundaries (i.e., walls and bases).

One eight well strip of the 96 well Assay Plate, which may be referred to as a "control strip," was used to provide controls, including four "nonstimulated" (NS) control wells and four "stimulated" control wells.

Another eight well strip of a 96 well Assay Plate, which may be referred to as a "test strip," was used for each sample to be tested. Four of the wells of each strip were designated as "nonstimulated" wells, while the other four wells of each strip were "stimulated" wells. Fifty microliters (50 μl) of Sample Diluent was introduced into each of the four "nonstimulated" wells of the control strip, while 25 μl of Sample Diluent was introduced into each of the "nonstimulated" wells of each test strip. Twenty-five microliters (25 μl) of Stimulant was introduced into each of the four "stimulated" wells of the control strip and into each of the four "stimulated" wells of each test strip.

In addition to the Sample Diluent or Stimulant, a 25 μl sample of one of the molecular weight fractions identified in EXAMPLE 1 was introduced into each of the eight wells of each test strip. More specifically, each of the molecular weight fractions of EXAMPLE 1 was reconstituted in Sample Diluent and diluted with a volume of Sample Diluent to provide three different concentrations that would ultimately, upon addition of a 25 µl sample to a well, respectively amount to the addition of 10 µg, 100 µg, and 1,000 µg of the dried powder to the well.

A 1:3 (blood: "Sample Diluent") dilution of a blood sample, which had been gently agitated to uniformly distribute its constituents, including white blood cells, was prepared. Seventy-five microliters (75 µl) of diluted blood was added to each well of each strip. The contents of the wells were then mixed (e.g., by placing the plate on a shaker plate for about 30 seconds), then incubated at a temperature of 37° C. in a 5% $CO_2$ environment for about 18 hours.

Once incubation was complete, the contents of the wells were again mixed (e.g., by placing the plate on a shaker plate for about three minutes). Thereafter, the solution including the Dynabeads® sample purification beads was mixed to homogenously suspend the Dynabeads® sample purification beads within the liquid by which they were carried (e.g., with a vortex). As noted above, the Dynabeads® sample purification beads in this example include magnetic beads coated with mouse monoclonal anti-human CD4 antibodies. Fifty microliters (50 µl) of the Dynabead® sample purification bead-carrying solution was added to each well of each strip.

The contents of the wells of each strip were again mixed (e.g., on a shaker plate for about 15 seconds), then allowed to set, or incubate, at room temperature for a duration of about 15 minutes. The process of mixing and incubation was then repeated. The mouse anti-human CD4 antibodies on the Dynabeads® sample purification beads bind only to white blood cells exhibiting the CD4 glycoprotein. During this incubation, CD4+ white blood cells, which include T helper cells, were immobilized by, or bound to, the mouse monoclonal anti-human CD4 antibodies on the Dynabeads® sample purification beads.

Following incubation, the contents of each well were mixed again (e.g., for about 15 seconds to about 30 seconds on a shaker plate) to resuspend the Dynabeads® sample purification beads. The contents of each well were then introduced into a magnetic field (e.g., by placing each eight well strip in a magnet tray available from Cylex), in accordance with the protocol set forth in the instructions that accompany the ImmuKnow™ assay. When subjected to the magnetic field, the Dynabeads® sample purification beads are pulled to one side of each well in which they are present. The remaining contents of the well may then be removed (e.g., aspirated with a pipette, etc.) and the beads and T helper cells washed one or more times (e.g., three times, each with 200 µl Wash Buffer) to substantially purify the same.

Two hundred microliters (200 µl) of Lysis Reagent was then added to each well. Following removal of the contents of each well from the magnetic field, the contents of each well (i.e., the Dynabeads® sample purification beads, cells attached thereto, and the Lysis Reagent) were mixed (e.g., for about five minutes on a plate shaker). The Lysis Reagent disrupted the membranes of the CD4+ cells that were immobilized by antibody on the Dynabeads® sample purification beads. Among other things, ATP was released from the lysed cells.

Once cell lysis was complete, the contents of each well were again subjected to a magnetic field, pulling the Dynabeads® sample purification beads within each well to one side of the well. A 50 µl sample was then transferred from each well to a corresponding well of the Measurement Plate.

In addition to transferring samples, several wells of the 96 well Measurement Plate were reserved for 50 µl samples of the various ATP concentrations of the Calibrator Panel solutions.

One hundred fifty microliters (150 µl) of the Luminescence Reagent was then added to each well of the Measurement Plate that included either a test sample or a sample of Calibrator Panel solution. The luminescence from each well was then measured. The measured luminescence from each well provides an indication of the amount of ATP present in that well. The amount of ATP present in each well is, in turn, indicative of an amount of metabolic activity within the cells (i.e., CD4+ cells) from which the contents of each well of the Measurement Plate. In the samples that were derived from cells that were nonspecifically stimulated with PHA, a relatively high level of ATP is expected to be present. The addition of an immune modulator (e.g., from one of the fractions identified in EXAMPLE 1) would increase or decrease, or modulate, the metabolic activity in CD4+ cells that was nonspecifically stimulated by PHA.

The results of such testing are set forth in the following table, with the illustrated numbers, representing the mean (average) amount of ATP produced by the white blood cells of each subset:

TABLE 1

| Sample | | Control | 10 µg per well | 100 µg per well | 1000 µg per well |
|---|---|---|---|---|---|
| 250 Da to 2,000 Da Colostrum fraction | Non-Stimulated (NS) | 14 | 52 | 50 | 37 |
| | Stimulated with PHA | 388 | 336 | 253 | 127 |
| | % reduction in PHA stimulation | | 13.4 | 34.8 | 67.3 |
| 2,000 Da to 4,000 Da Colostrum fraction | NS | 14 | 52 | 62 | 42 |
| | Stimulated with PHA | 388 | 388 | 377 | 339 |
| | % reduction in PHA stimulation | | 0 | 2.8 | 12.6 |
| 4,000 Da to 8,000 Da (includes TF) Colostrum fraction | NS | 14 | 69 | 50 | 46 |
| | Stimulated with PHA | 388 | 378 | 250 | 207 |
| | % reduction in PHA stimulation | | 2.6 | 35.6 | 46.6 |
| 8,000 Da to 12,000 Da Colostrum fraction | NS | 14 | 49 | 45 | 39 |
| | Stimulated with PHA | 388 | 337 | 237 | 181 |
| | % reduction in PHA stimulation | | 13.1 | 38.9 | 53.4 |
| 2,000 Da to 4,000 Da Egg fraction | NS | 14 | 49 | 33 | 44 |
| | Stimulated with PHA | 388 | 228 | 161 | 148 |
| | % reduction in PHA stimulation | | 41.2 | 58.5 | 61.9 |
| 4,000 Da to 8,000 Da (includes TF) Egg fraction | NS | 14 | 54 | 47 | 44 |
| | Stimulated with PHA | 388 | 354 | 230 | 158 |
| | % reduction in PHA stimulation | | 8.8 | 40.7 | 59.3 |

These data show that in the non-stimulated tests, where cells were not exposed to PHA, each of the 4,000 Da to 8,000 Da molecular weight fractions (from colostrum and egg), both of which are known to contain transfer factor, stimulated additional metabolic activity in the CD4+ white blood cells. These data confirm the ability of transfer factor to up-regulate cell-mediated immunity.

Conversely, the 4,000 Da to 8,000 Da colostrum and egg fractions down-regulated the nonspecific ability of PHA to stimulate metabolic activity in CD4+ cells. Since PHA is an artificial, nonspecific stimulant, the down-regulation of its activity by transfer factor, which participates in cell-mediated immunity, is not surprising. It is believed, and previous research has shown, that transfer factor helps balance, and even focus, immune activity by T-cells (e.g., by helping the cells "remember" their primary purpose, by reducing auto-immunity and associated disorders, while improving activity against undesirable entities, such as infection of a subject's body by microorganisms (bacteria, viruses, etc.), etc.). The down-regulation of PHA-stimulated activity by T-cells appears to confirm this role of transfer factor in cell-mediated immunity.

Similar results were seen in a number of other molecular weight fractions that do not include transfer factor, including the 250 Da to 2,000 Da colostrum fraction (both up-regulation and down regulation), the 2,000 Da to 4,000 Da colostrum fraction (up-regulation), and the 2,000 Da to 4,000 Da egg fraction (up-regulation and down-regulation). The 8,000 Da to 10,000 Da colostrum fraction also caused up-regulation of activity in CD4+ white blood cells that were not stimulated with PHA and down-regulation of PHA stimulation of metabolic activity in CD4+ white blood cells.

These data establish that immune modulators other than transfer factor are present in at least the 250 Da to 2,000 Da colostrum fraction, the 2,000 Da to 4,000 Da colostrum fraction, and the 2,000 Da to 4,000 Da egg fraction. The immune modulation capabilities of the "nanofraction molecules" present in each of these fractions has been at least partially confirmed by the experiment that is set forth in EXAMPLE 3.

Example 3

A second series of assays of activity induced in a healthy individual's white blood cells exhibiting the CD3 glycoprotein (i.e., CD3+ cells), which are known to include all T-cells, including so-called "T memory" cells. Specifically, Cylex's T-Cell Memory™ assay was used. The protocol of Cylex's T-Cell Memory™ assay is very similar to that set forth in EXAMPLE 2, with the following exceptions: 25 μl of the Stimulant, which included Concanavalin A (ConA) instead of PHA, was only introduced into the "stimulated" wells of the control strip, while 25 μl of a 1:10 dilution of cytomegalovirus (CMV) vaccine was added to the "stimulated" wells of each test strip (for a final, per well dilution of 1:50); mouse anti-human CD3 antibodies were immobilized to the surfaces of magnetic beads (per instructions accompanying the T-Cell Memory™ test kit) to prepare the Dynabeads® sample purification beads; and the Dynabeads® sample purification beads were added to the blood samples, Sample Diluent, Stimulant (if any), and sample fraction (if any) before the initial incubation.

In the T-Cell Memory™ assay, antigen is used in place of a mitogen (e.g., PHA) so that the ability of the T memory cells to recognize a particular antigen may be evaluated. Notably, the intensity of the light emitted from each well of the Measurement Plate is less, as T memory cells make up only a portion of the cells that have been bound to antibody molecules of the Dynabeads®.

The results of these assays are set forth in the following table, with the illustrated numbers representing the mean (average) amount of ATP produced by the white blood cells for each sample (and amount) tested:

TABLE 2

| Sample | | Control | 10 μg | 100 μg | 1000 μg |
|---|---|---|---|---|---|
| 250 Da to 2,000 Da Colostrum fraction | Non-Stimulated (NS) | 12 | 14 | 12 | 17 |
| | Stimulated with CMV | 316 | 468 | 338 | 345 |
| | % increase in CMV stimulation | | 48.1 | 7.0 | 9.2 |
| 2,000 Da to 4,000 Da Colostrum fraction | NS | 12 | 15 | 12 | 15 |
| | Stimulated with CMV | 316 | 501 | 503 | 440 |
| | % increase in CMV stimulation | | 58.5 | 59.1 | 39.2 |
| 4,000 Da to 8,000 Da (includes TF) Colostrum fraction | NS | 12 | 22 | 16 | 19 |
| | Stimulated with CMV | 316 | 473 | 476 | 475 |
| | % increase in CMV stimulation | | 49.7 | 50.6 | 50.3 |
| 8,000 Da to 12,000 Da Colostrum fraction | NS | 12 | 14 | 18 | 26 |
| | Stimulated with CMV | 316 | 453 | 404 | 370 |
| | % increase in CMV stimulation | | 43.4 | 27.8 | 17.1 |
| 2,000 Da to 4,000 Da Egg fraction | NS | 12 | 26 | 61 | 108 |
| | Stimulated with CMV | 316 | 305 | 349 | 350 |
| | % increase in CMV stimulation | | −3.5 | 10.4 | 10.8 |
| 4,000 Da to 8,000 Da (includes TF) Egg fraction | NS | 12 | 34 | 39 | 108 |
| | Stimulated with CMV | 316 | 310 | 280 | 381 |
| | % increase in CMV stimulation | | −1.9 | −11.4 | 20.6 |

The data obtained from the testing conducted in this EXAMPLE 3 demonstrate that, in the presence of an antigen (i.e., a specific stimulant, as opposed to the nonspecificity of a mitogen, such as ConA or PHA), the three non-transfer factor-containing colostral fractions enhance the activity of the tested T memory cells to CMV to a degree that is comparable to (the 10 μg samples of the 250 Da to 2,000 Da and 8,000 Da to 12,000 Da colostrum fractions) or exceeds (the 10 μg and 100 μg samples of the 2,000 Da to 4,000 Da colostrum fraction) the ability of the comparably sized samples of the 4,000 Da to 8,000 Da, transfer factor-containing colostrum fraction to enhance the activity of the tested cells when exposed to CMV.

Example 4

Another set of assays was conducted to determine whether or not either the nanofraction immune modulator molecules (i.e., the immune modulators of the 2,000 Da to 4,000 Da colostrum fraction) or the transfer-factor containing fraction (i.e., the 4,000 Da to 8,000 Da colostrum fraction) could modulate (e.g., enhance) the immune memory of a subject who had recently been exposed to a high dose of a particular antigen. Specifically, a blood sample was obtained from an individual who had been exposed to an influenza virus, which causes a systemic infection, and suffered from influenza symptoms for four weeks.

The assay was conducted in the manner described in EXAMPLE 3, using the Cylex T-Cell Memory™ assay in accordance with the instructions provided with that assay and set forth in EXAMPLE 3, except an influenza antigen, in the form of 1:25 dilution of the influenza vaccine manufactured by Aventis Pasteur of Paris, France, for the 2006-2007 flu season (for a final, per well dilution of 1:125), was used in place of the CMV vaccine of EXAMPLE 3.

The results from that assay are set forth in the following table:

TABLE 3

| Sample | | Control | 10 µg | 100 µg | 1000 µg |
|---|---|---|---|---|---|
| 2,000 Da to 4,000 Da Colostrum fraction | NS | 4 | 10 | 3 | 4 |
| | Stimulated with influenza antigen | 827 | 1003 | 906 | 936 |
| | ConA | 694 | | | |
| | % increase in influenza antigen stimulation | | 21.3 | 9.6 | 13.2 |
| 4,000 Da to 8,000 Da (includes TF) Colostrum fraction | NS | 4 | 36 | 24 | 11 |
| | Stimulated with influenza antigen | 827 | 989 | 997 | 830 |
| | ConA | 694 | | | |
| | % increase in influenza antigen stimulation | | 19.6 | 20.6 | 0.4 |

The results shown in TABLE 3 (which are also shown graphically in FIG. 1) indicate that, when T memory cells of a subject who has recently been exposed to a particular antigen are exposed to that antigen, particularly in the presence of nanofraction molecules or transfer factor, activity of the CD3+ memory T-cells increases significantly. In fact, relatively small amounts of nanofraction molecules and of transfer factor caused an increase of about 20% in T memory cell activity. In fact, it appears that the immune modulators of the 2,000 Da to 4,000 Da fraction are about as effective as the transfer factor and any other molecules present in the 4,000 Da to 8,000 Da fraction in modulating the activity of the tested cells.

The results from EXAMPLES 1-4 indicate that immune modulators having molecular weights in the 250 Da to 2,000 Da, 2,000 Da to 4,000 Da, and 8,000 Da to 12,000 Da ranges are effective in modulating immune activity of various types of T-cells. Thus, by administering such immune modulators or preparations or compositions including the immune modulators to a subject, the subject's cell-mediated immunity may be modulated.

Based on these results, a process was developed for producing various dietary supplements (e.g., from (bovine) colostrum, (chicken) egg, etc.) that include molecules of a predetermined MWCO. For example, and not by way of limitation, a liquid preparation of a source of nanofraction immune modulators, from which at least macroscopic particles (e.g., colostrum/milk solids, egg shells and membranes, etc.) (e.g., by phase separation, filtration processes, etc.) have been removed may be forced through a filter with pores that are sized to provide the predetermined upper MWCO. As a nonlimiting example, a filter that provides a molecular weight cutoff of about 3,000 Da may be used. Alternatively, dialysis processes, which include use of dialysis membranes having pores that provide the desired MWCO, may be used. The use of such processes provides a "nanofraction" from which larger molecules, including transfer factor, antibodies, and a variety of other molecules having molecular weights of greater than about 3,000 Da, are excluded (e.g., colostrum, chicken and various powdered compositions were produced. The filtrate (i.e., the portion of the liquid that has passed through the filter) may then be further processed by known techniques (e.g., freeze drying, spray drying, evaporation to form a more concentrated liquid, incorporation into a gel, etc.). The resulting "nanofraction product" may then be used alone or incorporated into other compositions.

It is believed that by including nanofraction molecules, even in very small amounts, in preparations that also include transfer factor (and which may also include baseline levels (i.e., those levels already present in the source (e.g., colostrum, egg, etc.) from which transfer factor is obtained), the resulting compositions will down-regulate undesired activity by T-cells (e.g., autoimmunity and associated disorders, etc.), while improving, or up-regulating, desired T-cell activity. The nanofraction-and-transfer factor compositions that are set forth in TABLES 4 and 5 were developed.

TABLE 4

COMPOSITION A

| Ingredient | Relative Amount (by weight) |
|---|---|
| Bovine Colostrum fraction, upper MWCO 10,000 Da (spray dried) | 68% |
| Bovine Colostrum fraction, upper MWCO 3,000 Da (nanofraction) (spray dried) | 2% |
| Chicken Egg Yolk (spray dried) | 30% |

The composition of TABLE 4 may also be referred to as an "immune modulating component." Such an "immune modulating component" may consist essentially of a combination of sources of immune modulators (including sources of nanofraction immune modulators) or extracts of immune modulator sources, such as those listed in TABLE 4, or it may include other ingredients.

Likewise, a composition that incorporates teachings of the present invention may consist essentially of an "immune modulating component," such as that disclosed in TABLE 4, or it may include other ingredients, as set forth in TABLE 5.

TABLE 5

COMPOSITION B

| Ingredient | Amount (per serving, serving size = one capsule) |
|---|---|
| Composition A | 150 mg |
| Zinc (as monomethionine) | 5 mg |
| Cordyvant ™ Proprietary Polysaccharide Complex | 440 mg |
| IP-6 (Inositol hexaphosphate) | |
| Soya bean Extract (phytosterols) | |
| *Cordyceps sinensis* (7% cordyceptic acids) | |
| Beta-Glucan (from baker's yeast) (*Saacharomyces cerevisiae*) | |
| Beta-Glucan (from Oat) (*Avena sativa*) | |
| *Agaricus blazeii* Extract | |
| Mannans (from *Aloe vera*) (leaf) | |
| Olive Leaf Extract (*Olea europaea*) | |
| Maitake Mushroom (*Grifola frondosa*) (whole plant) | |
| Shiitake Mushroom (*Lentinus edodes*) (whole plant) (5:1 extract) | |

A composition according to the present invention may be embodied as a liquid (e.g., into the RioVida® drink available from 4Life Research, LC, of Sandy, Utah), a powder (which may include additional ingredients to provide a desirable flavor, dissolution properties, and the like), a tablet (which additionally includes other ingredients, such as binders (e.g., starch) and the like, a gel (in which gelatin or other ingredients may be added), or in any other suitable form. It should be understood that, for purposes of this disclosure, the additional ingredients that are used to manufacture such embodiments of a composition of the present invention may, for purposes of this disclosure, merely be considered to be optional and nonessential to the composition, unless otherwise required by an appended claim.

Example 5

Blood was collected from an individual who had been suffering from shingles (varicella zoster virus (VZV) infection) symptoms for about four weeks. The blood was then assayed using the ImmuKnow™ assay in the manner described in EXAMPLE 2, with the sample fractions of EXAMPLE 2 having been replaced with the following: (a) a control that included no immune modulators; (b) a colostrum fraction having a MWCO of about 3,000 Da that had been spray dried; (c) Transfer Factor XF®, which is currently available from 4Life Research and includes a bovine colostrum extract with an upper MWCO of about 10,000 Da, was added; (d) the composition in TABLE 4, which is labeled as "Composition A"; and (e) the composition of TABLE 5, which is labeled as "Composition B." Each of (b) through (e) was reconstituted in the Sample Diluent that accompanied the ImmuKnow™ assay, and diluted to a concentration that resulted in a final, per-well concentration of 1 mg/ml once blood samples and all other liquids had been added to each well.

The results from those assays are set forth in the following table:

TABLE 6

|  | Control | Nano-fraction | TF XF | Composition A | Composition B |
|---|---|---|---|---|---|
| Non-Stimulated (NS) | 26 | 35 | 77 | 47 | 19 |
| Stimulated with PHA | 220 | 234 | 150 | 140 | 27 |

Figure 2:
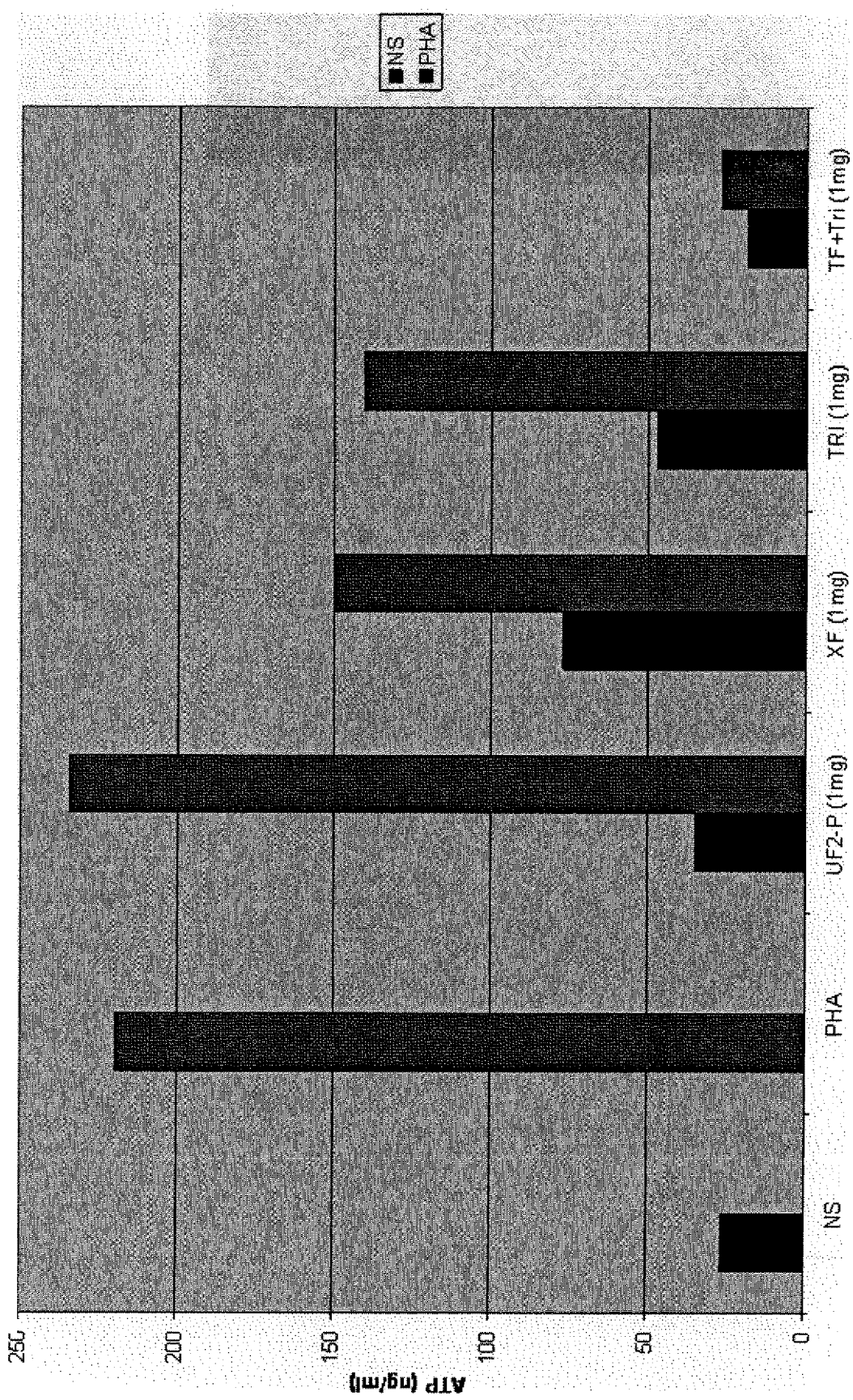

These results also appear in the graph of FIG. 2.

It is reiterated that these results were obtained at a point in time (about four weeks following initial infection; i.e., during convalescence) where, in the absence of stimulation, T helper (CD4+) cell activity is expected to decrease, although a large number of T helper cells remain in the subject's blood. T helper cell activity was stimulated only slightly, in the absence of the nonspecific stimulant PHA, by the nanofraction, TF XF, and Composition A, and does not appear to have been stimulated by Composition B. The nonspecific stimulation of T helper cells by PHA was, however, reduced significantly by the TF XF and Composition A, and to an even larger extent by the Composition B, as might be expected from the results of EXAMPLE 2, as set forth in TABLE 1.

Example 6

At an earlier point in time (about one week following the onset of shingles symptoms), it would be expected that T memory cells, although not present in the subject's blood in large concentrations due to the localized nature of the VZV infections that cause shingles (i.e., relatively low blood titers of VZV), would have already recognized the VZV infection and be readily stimulated by the presence of VZV antigen. Accordingly, a T-Cell Memory™ assay was conducted to determine the effects of the nanofraction, TF XF, Composition A, and Composition B on T memory cells from blood from the same patient as that tested in EXAMPLE 5. The protocol set forth in EXAMPLE 3 was followed, with the following exceptions: VZV vaccine, which had been diluted 1:10, was used in place of CMV vaccine (for a final, per well dilution of 1:50); and the sample fractions of EXAMPLE 3 were replaced with the control and immune modulators used in EXAMPLE 5, with each immune modulator having been diluted to a final, per-well concentration of 100 µg/ml.

The following table sets forth the results of the assay:

TABLE 7

|  | Control | Nano-fraction | TF XF | Composition A | Composition B |
|---|---|---|---|---|---|
| Non-Stimulated (NS) | 1 | 2 | 13 | 27 | 51 |
| Stimulated with VZV | 1 | 5 | 30 | 32 | 69 |
| Stimulated with ConA | 288 |  |  |  |  |

Figure 3:
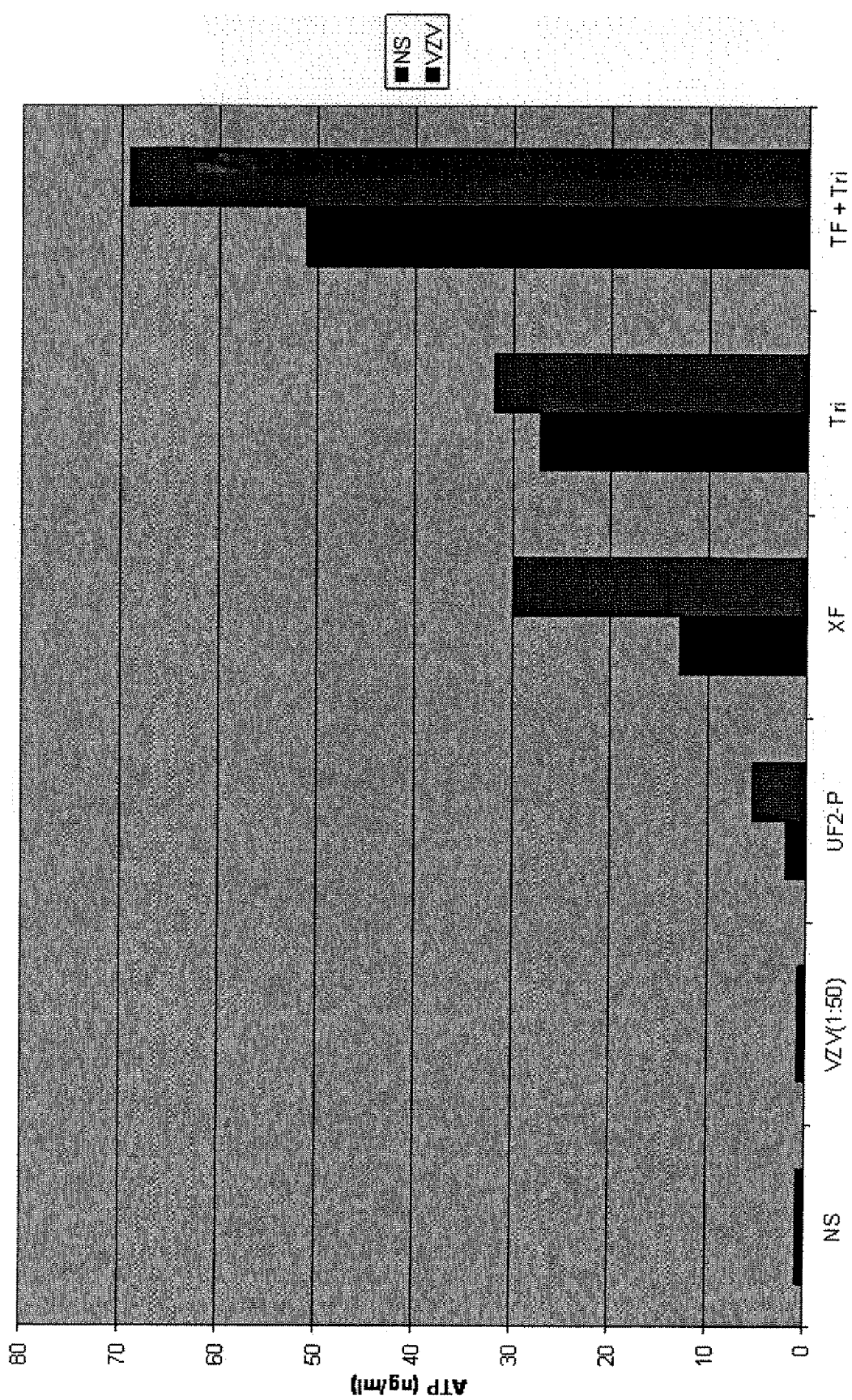

This data is also depicted graphically in FIG. 3.

As expected, transfer factor, which is present in TF XF, stimulated activity by the T memory cells. The addition of a small amount of extra nanofraction molecules to the transfer factor significantly increased the activity of T memory cells, both with and without additional VZV stimulation. Thus, the results of EXAMPLES 5 and 6 confirm that the addition of extra nanofraction molecules to preparations that also include transfer factor, even in very small amounts, will down-regulate undesired activity by T-cells (e.g., autoimmunity and associated disorders, etc.), while improving, or up-regulating, desired T-cell activity.

Example 7

In another study, which was conducted to determine the abilities of various compositions, including the compositions including transfer factor and extra nanofraction molecules set forth in TABLES 4 and 5, to stimulate natural killer (NK) cell activity against the human erythroblast leukemia cell line K-562, which is sensitive to NK cells, were evaluated. Accordingly, the NK cells are also referred to herein as "effector cells," while the K-562 cells are also referred to herein as "tumor cells" and as "target cells." Specifically, MTT Assay technology was used, in which 3-(4,5-Dimethylthiazol-2-yl)-2,5-diphenyltetrazolium bromide (MTT), which is yellow, is reduced to formazan, which is purple, by reductase enzymes in the active mitochondria of living cells. Just prior to analysis of cytotoxicity, a solution (e.g., dimethyl sulfoxide, sodium dodecyl sulfate (SDS) in dilute hydrochloric acid (HCl), etc.) that will dissolve formazan is added to each well. Spectrophotometry, in which the amount of light of a certain wavelength (e.g., a wavelength in the range of about 500 nm to about 600 nm) absorbed by the solution in each well is measured, is then used to determine the numbers of living cells in the assayed wells, relative to the number of living cells in one or more control wells into which no test compositions were added.

The compositions that were evaluated included Transfer Factor Advanced™, available from 4Life Research; Transfer Factor Plus Advanced™, also available from 4Life Research; Composition A, which includes both transfer factor and an elevated amount of nanofraction molecules; Composition B, which includes transfer factor, an elevated amount of nanofraction molecules, and other ingredients that are believed to enhance immune system activity; nanofraction molecules from bovine colostrum; nanofraction molecules from chicken eggs; and interleukin-2 (IL-2), available under the trade name Proleukin from Chiron of the Netherlands, which is known to enlist NK cells against cancer cells.

Blood was obtained from five healthy donors. Known processes were used to isolate white blood cells from other constituents of the blood. Known density gradient centrifugation techniques (e.g., using a Histopaque® density gradient available from Sigma-Aldrich Corporation of St. Louis, Mo.) were used to isolate mononuclear cells, including NK cells, from other types of white blood cells. The mononuclear cells were introduced into RPMI 1640 growth medium with 10% fetal calf serum (FCS). Equal volumes of this mixture, including a concentration of about 60,000 white blood cells in 100 µl of culture medium, were introduced into different wells of a standard 96-well plate. Reconstituted samples of the transfer factor and/or nanofraction molecule-containing compositions identified above, each having a concentration of 0.100 mg powder to 1 ml sterile, deionized water, were each added to three different wells containing the white blood cells and growth medium, for a total of eighteen wells. In addition, 1,000 IU/ml IL-2 were introduced into three positive control wells containing the mononuclear cell-growth medium mixture. Three negative control wells included only the mononuclear cell-growth medium mixture, with no immune modulators. Three effector cell-only negative control wells also included only the mononuclear cell-growth medium mixture, while three target cell-only negative control wells included only 100 µl of growth medium.

The mononuclear cells were incubated with their respective immune modulation compositions (except for the three negative control wells) in the presence of 5% $CO_2$ at a temperature of 37° C. and 100% humidity for 48 hours.

Following incubation, about 30,000 K-562 cells were introduced into each well, except for the three effector cell-only negative control wells, that contained mononuclear cells and growth medium. The 96-well plate and the mixtures in its wells were again incubated in the presence of 5% $CO_2$ at a temperature of 37° C. and 100% humidity for 48 hours.

The MTT solution, having a concentration of 5 mg MTT/ml Henk's saline solution, was prepared in accordance with known, standard techniques. Twenty microliters (20 µl) of the MTT solution was introduced into each mononuclear cell-growth medium-tumor cell-containing well of the 96-well plate. The plate and the contents of its wells were again incubated in the presence of 5% $CO_2$ at a temperature of 37° C. and 100% humidity, this time for about four hours.

Following this final incubation, the 96-well plate was centrifuged at about 1,500 rpm for about five minutes. Thereafter, the supernatant (liquid) was removed from each well, and 150 µl of dimethylsulfoxide (DMSO) was introduced into to each mononuclear cell and tumor cell-containing well. A spectrophotometer was then used to measure the optical density, at a wavelength of 540 nm, of each cell-containing well. The measured optical density was then used to determine the cytotoxic index (%) (CI (%)) of the NK cells, as activated by each tested substance, using the following formula:

$$CI\ (\%) = [1-(OD_{e+t}-OD_e)/OD_t] \times 100,$$

where $OD_{e+t}$ is optical density of each test well corresponding to a tested composition, including the IL-2 of the positive control, $OD_e$ is the average optical density of the three effector cell-only negative control wells, and $OD_t$ is the average optical density of the three target cell-only negative control wells. The CI(%) represents the percentage of target cells that have been killed by NK cells in each well that also contained a tested immune modulation composition. The results are presented in the following table:

TABLE 8

| Immune Modulation Composition | CI (%) | Relative Activity |
|---|---|---|
| Transfer Factor Advanced ® | 43.1 | 55 |
| Transfer Factor Plus Advanced ™ | 38.5 | 49 |
| Composition A | 60.3 | 77 |
| Composition B | 57.9 | 74 |
| Nanofraction molecules, colostrum | 77.9 | 100 |
| Nanofraction molecules, egg | 68.7 | 88 |
| IL-2 | 77.0 | 84 |

Figure 4:
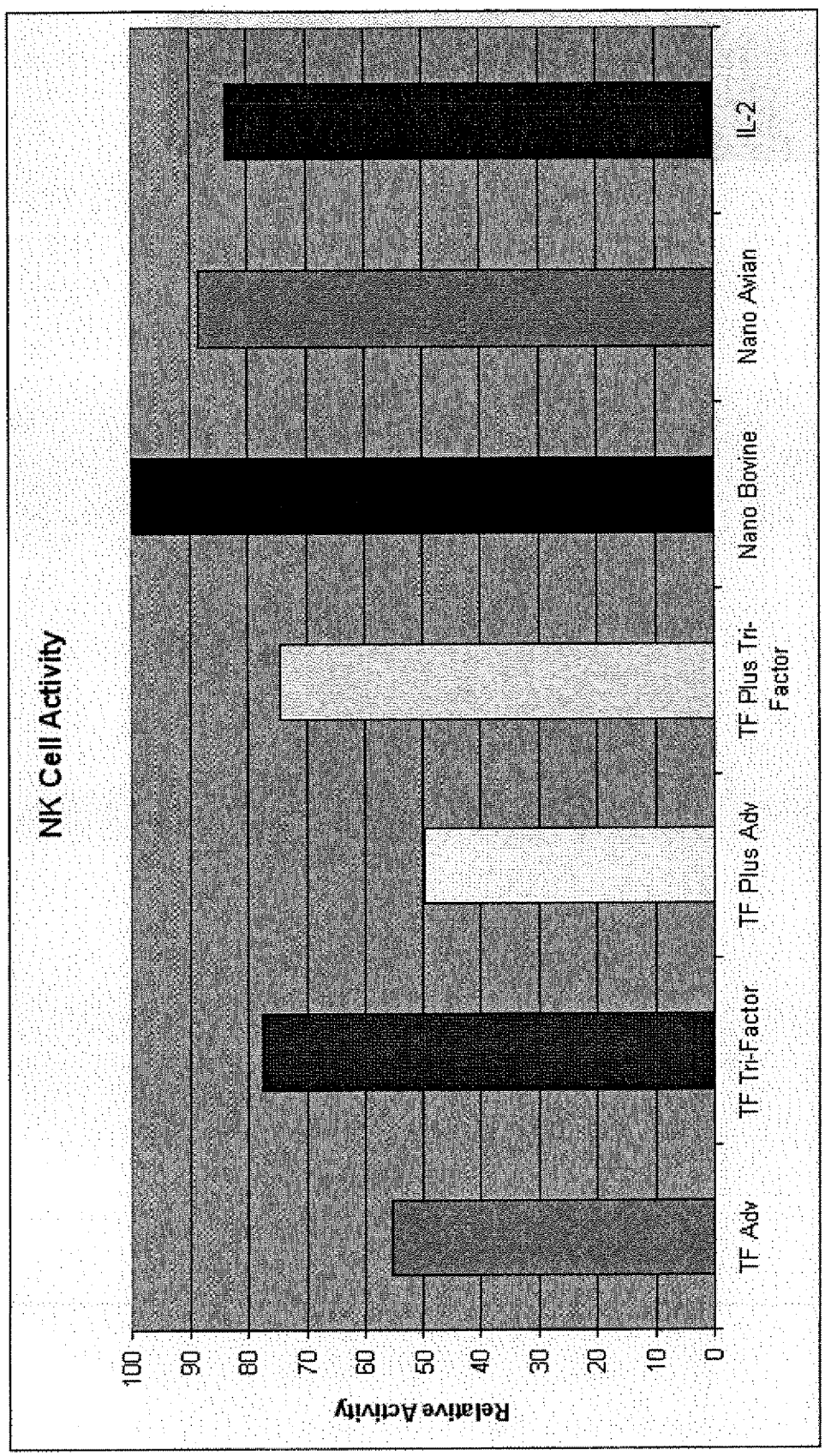

These data, which are also depicted in the chart of FIG. 4, show that compositions including nanofraction molecules, particularly those from bovine colostrum, are about as effective as or more effective than IL-2 at eliciting NK cell activity against K-562 tumor cells, while compositions that include transfer factor from colostrum and eggs and nanofraction molecules from colostrum (i.e., Composition A and Composition B) activate NK cells more effectively than compositions that lack nanofraction molecules.

By adding as little as 2% more nanofraction molecules, by weight, to a composition that includes transfer factor, the nanofraction molecules may boost action by nonspecific components (e.g., NK cells) of the cell-mediated portion of a subject's immune system, complementing the ability of transfer factor to elicit activity by antigen-specific components of the cell-mediated portion of the subject's immune system.

When considered together, the results of EXAMPLES 5 through 7 demonstrate that transfer factors regulate and prime T helper cells, which enable a subject's immune system to respond more quickly and efficiently to pathogens and other undesired entities. In addition, EXAMPLES 5 through 7 illustrate that transfer factor may enhance the activity of T memory cells.

EXAMPLES 5 through 7 also show that the addition of extra nanofraction immune modulator molecules to compositions that include transfer factor may fortify and enhance the immune modulation (e.g., of T helper cells, T memory cells, and NK cells) of transfer factor and of existing compositions that include transfer factor.

A method of modulating the cell-mediated immunity of a subject includes administering (e.g., enterally, parenterally, etc.) a composition including nanofraction molecules to the subject. The nanofraction molecules may be administered alone, or as part of a composition that consists essentially of nanofraction molecules, or they may be administered with a composition (e.g., a composition such as that set forth in TABLE 4 or TABLE 5) that includes transfer factor. Administration may occur on a regular basis in an effort to maintain an overall balance in the subject's cell-mediated immunity, or it may be effected in response to an infection, an autoimmune disorder, tissue transplant, or another event that affects (activates or suppresses) the cell-mediated immunity of the subject.

Administration of compositions that include nanofraction immune modulator molecules in accordance with teachings of the present invention is believed to modulate cell-mediated immune activity based on physiological need. For example, undesired cell-mediated immune activity (e.g., autoimmunity, etc.) may be reduced. As another example, the ability of T-cells to remove undesirable pathogens, as well as other undesirable entities, such as cancer cells and other aberrant or mutated cells, from the body of a subject (e.g., by activating T helper (CD4+) cells, which in turn activate natural killer (NK) cells, by increasing antigen-specific immunity by enabling T memory cells, etc.) may also be focused and enhanced, particularly when transfer factor is administered with an additional amount of nanofraction immune modulator molecules.

Although the foregoing description contains many specifics, these should not be construed as limiting the scope of the present invention, but merely as providing illustrations of some of the presently preferred embodiments. Similarly, other embodiments of the invention may be devised which do not depart from the spirit or scope of the present invention. Features from different embodiments may be employed in combination. The scope of the invention is, therefore, indicated and limited only by the appended claims and their legal equivalents, rather than by the foregoing description. All additions, deletions and modifications to the invention as disclosed herein which fall within the meaning and scope of the claims are to be embraced thereby.

What is claimed:

1. A composition comprising an immune modulating component consisting of:
   a first fraction of a first quantity of bovine colostrum, the first fraction having a first upper molecular weight cutoff of about 10,000 Da;
   a second fraction of a second quantity of bovine colostrum, the second quantity being separate from the first quantity, the second fraction having a second upper molecular weight cutoff of about 4,000 Da obtained by separating molecules having molecular weights at and below the second upper molecular weight cutoff from molecules having molecular weights above the second upper molecular weight cutoff; and
   egg yolk,
   the first fraction, the second fraction, and the egg yolk being combined with one another.

2. The composition of claim 1, wherein:
   the first fraction includes transfer factor and immune modulators; and
   the second fraction includes immune modulators.

3. The composition of claim 1, wherein the egg yolk is chicken egg yolk.

4. The composition of claim 1, wherein the egg yolk is in a dried form.

5. The composition of claim 4, wherein the first fraction and the second fraction are in dried forms.

6. The composition of claim 5, wherein:
   the first fraction makes up about 68% of the total weight of the immune modulating component;
   the second fraction makes up about 2% of the total weight of the immune modulating component; and
   the egg yolk makes up about 30% of the total weight of the immune modulating component.

7. The composition of claim 1, wherein the first fraction is obtained by separating molecules having molecular weights at and below the first upper molecular weight cutoff from molecules having molecular weights above the first upper molecular weight cutoff.

* * * * *